(12) United States Patent
Wakatsuki

(10) Patent No.: US 10,113,150 B2
(45) Date of Patent: Oct. 30, 2018

(54) ENGINEERED CARDIAC TISSUES AND METHODS OF USING THEM

(75) Inventor: Tetsuro Wakatsuki, McFarland, WI (US)

(73) Assignee: InvivoSciences, Inc., Madison, WI (US)

( * ) Notice: Subject to any disclaimer, the term of this patent is extended or adjusted under 35 U.S.C. 154(b) by 0 days.

(21) Appl. No.: 14/124,198

(22) PCT Filed: Jun. 6, 2012

(86) PCT No.: PCT/US2012/041048
§ 371 (c)(1),
(2), (4) Date: Dec. 5, 2013

(87) PCT Pub. No.: WO2012/170490
PCT Pub. Date: Dec. 13, 2012

(65) Prior Publication Data
US 2014/0094388 A1     Apr. 3, 2014

Related U.S. Application Data

(60) Provisional application No. 61/493,695, filed on Jun. 6, 2011.

(51) Int. Cl.
| | |
|---|---|
| *C12N 5/00* | (2006.01) |
| *C12N 5/02* | (2006.01) |
| *C12N 5/071* | (2010.01) |
| *C12N 5/077* | (2010.01) |
| *G01N 33/50* | (2006.01) |

(52) U.S. Cl.
CPC ......... *C12N 5/0697* (2013.01); *C12N 5/0627* (2013.01); *C12N 5/0657* (2013.01); *G01N 33/5082* (2013.01); *C12N 2502/1323* (2013.01); *C12N 2506/02* (2013.01)

(58) Field of Classification Search
CPC .................................................... C12N 5/067
USPC ......................................................... 435/373
See application file for complete search history.

(56) References Cited

U.S. PATENT DOCUMENTS

| | | |
|---|---|---|
| 5,856,153 A | 1/1999 | Cayla |
| 7,449,306 B2 | 11/2008 | Elson et al. |
| 8,071,381 B2 | 12/2011 | Elson et al. |
| 2008/0038812 A1 | 2/2008 | Elson et al. |
| 2009/0169521 A1 | 7/2009 | Levenberg et al. |
| 2009/0202977 A1 | 8/2009 | Ott et al. |
| 2011/0118143 A1 | 5/2011 | Wakatsuki |

OTHER PUBLICATIONS

Anderson, 2007, Molecular Therapy, 15:20027-2036.*
Camelitti (2005; Cardiovascular Research, 65:40-51).*
Stojkovic (2005, Stem Cells 23: 306-314).*
Asnes, C.F. et al., "Reconstitution of the Frank-Starling mechanism in engineered heart tissues," (2006) Biophysical J. 91:1800-1510.
Boateng, S.Y. et al., "Inhibition of fibroblast proliferation in cardiac myocyte cultures by surface microtopography", (2003) Am J. Physiol Cell Physiol 285:C171-C182.
Gerecht-Nir, S. et al., "Biophysical regulation during cardiac development and application to tissue engineering", (2006) Int J Dev Biol 50:233-243.
Guo, X.M. et al., "Creation of engineered cardiac tissue in vitro from mouse embryonic stem cells," (2006) Circulation 113(18):2229-2237.
Parker, K.K. et al., "Extracellular matrix, mechanotransduction and structural hierarchies in heart tissue engineering," (2007) Philos Trans R Soc Lond B Biol Sci 362(1484):1267-1279.
Schaaf, S. et al., "Human engineered heart tissue as a versatile tool in basic research and preclinical toxicology," (2011) PLoS ONE 6(10):e26397.
Tulloch, N.L. et al., "Growth of engineered human myocardium with mechanical loading and vascular coculture," (2011) Circulation Research 109:47-59.
Zimmermann, W.-H. et al., "Engineered heart tissue for regeneration of diseased hearts," (2004) Biomaterials 25:1639-1647.
International Search Report and Written Opinion for International Patent Application No. PCT/US2012/041048 dated Oct. 16, 2012 (11 pages).

* cited by examiner

*Primary Examiner* — Valarie E Bertoglio
(74) *Attorney, Agent, or Firm* — Andrus Intellectual Property Law, LLP

(57) ABSTRACT

Engineered cardiac tissues are provided herein. The tissues include cardiomyocyte cells derived from a pluripotent cell, fibroblast cells and extracellular matrix components. Methods of using the tissues described herein are also provided.

13 Claims, 17 Drawing Sheets

Scaffold (20)

A.

B.

C.

ENGINEERED CARDIAC TISSUES AND METHODS OF USING THEM

CROSS-REFERENCE TO RELATED APPLICATIONS

This patent application is a national stage filing under 35 U.S.C. 371 of International Application No. PCT/US2012/041048, filed Jun. 6, 2012, which claims the benefit of priority of U.S. Provisional Patent Application No. 61/493,695, filed Jun. 6, 2011, both of which are incorporated herein by reference in their entirety.

INTRODUCTION

Hundreds of protein kinase inhibitors are in the pipeline of drug development. Remarkable recent successes in cancer therapy with kinase inhibitors triggered the current boom in developing kinase cancer drugs. Unfortunately many of the drug-target kinases also regulate and maintain physiological cardiac functions. Therefore, the cardio-toxicity of widely prescribed inhibitors including imatinib mesylate (Gleevec) became apparent. Moreover, childhood cancer survivors will develop cardiomyopathy more often (5-10×) than healthy counterparts due to an unexpected anthracycline cardio-toxicity. Cardio-toxicity of the cancer drugs has been tested rigorously by FDA-recommended protocols including assessment of QT-interval prolongation (arrhythmogenicity). However, the approved cancer drugs were later discovered to induce cardiomyopathy without QT prolongation. Abnormality in cardiac contractility is one of the clear signs of cardio-toxicity. Therefore, a reliable system for monitoring cardiac contractility that can predict general cardio-toxicity of drug candidates is critically needed. Although animal studies should predict general cardio-toxicity, models based on human cells will be desirable to test for human-specific cardio-toxicity during the early stages of drug discovery.

SUMMARY

Engineered cardiac tissues and methods of using these tissues are provided herein. The engineered cardiac tissues include cardiomyocyte cells derived from a pluripotent cell, fibroblast cells and extracellular matrix components. The growth of the fibroblast cells in the tissue may be capable of being limited. The tissue contracts coherently and may also contract synchronously with electrical pacing by an external electrical stimulator. The cardiac tissues nay be formed on a scaffold support disposed within a well such that the tissue is suspended from the scaffold support above the bottom of the well. The tissue may be formed on the scaffold support without a fastener to facilitate tissue adhesion.

In another aspect, methods of evaluating the effects of an agent on cardiac performance are provided. The methods include contacting the tissues described herein with the agent and comparing the cardiac performance of the tissue after contact with the agent to the cardiac performance of a control. The control may be the tissue prior to contact with the agent.

BRIEF DESCRIPTION OF THE DRAWINGS

FIG. 3A is a top elevation view of the scaffolds. FIG. 3B is a side elevation view of the scaffolds, FIG. 3C is a side elevation view of one way of connecting several scaffolds to each other for ease of use in high throughput applications.

FIG. 7A is a set of photographs showing stretching of EHTs to measure its twitch force. FIG. 7B is a graph in which the slope of the line denotes cardiac contractility. The twitch force profile and dF/dt are depicted in FIGS. 7C and 7D respectively. The twitch force is shown in FIG. 7E and TMRE stained mito-potential measured using a plate reader is shown in FIG. 7F. As increasing concentrations of mito-potential decoupler, DNP, were added twitch force was reduced as expected.

FIG. 10(A) shows isoform specific knockdown of ROCK1 or ROCK2 expression for 1 and 6 weeks by the appropriate shRNAs. FIG. 10B shows ECM and cell adhesion related gene expression. FIGS. 10C and D show ROCK2 specific down-regulation of αSM actin and procollagen type I respectively.

FIG. 11A shows the stress relaxation at different stretch levels (see 11B-11D for enlarged response).

FIG. 15A shows EHTs fabricated with only myocytes. FIG. 15B shows EHTs fabricated by mixing cardiomyocytes with mFBs. Coherent cardiac contraction was only achieved by EHTs with both myocytes ad mFBs.

DETAILED DESCRIPTION

Figure 1:
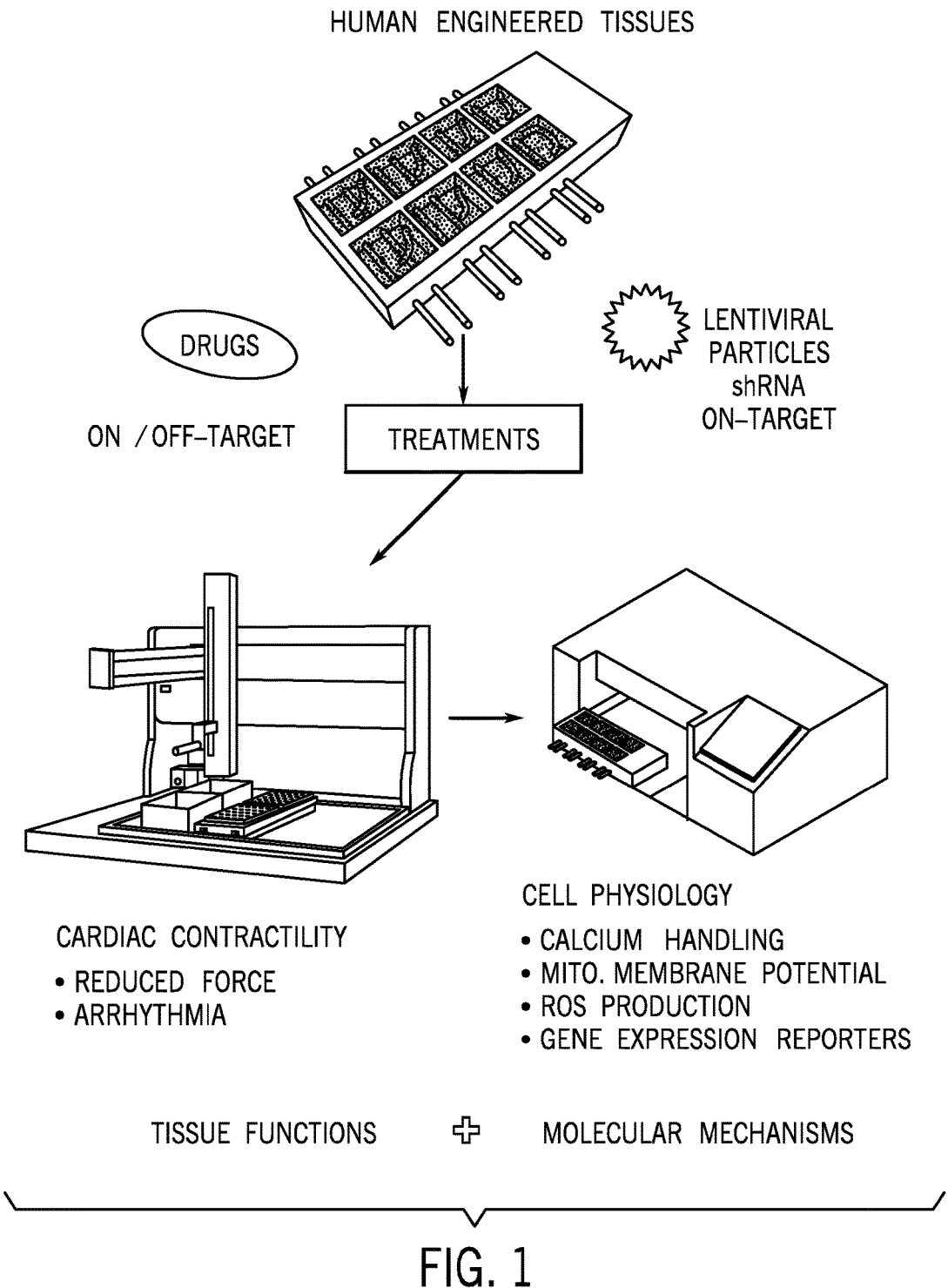
FIG. 1 is a schematic depicting multi-parameter cardio-toxicity profiling. Drug or shRNA induced effects on cardiac contractility and other physiological parameters of cardiac cells will be monitored simultaneously using automated assay system.

The engineered heart tissues (EHT) and methods described herein will provide an in vitro system for modeling and understanding cardiac function. An in vitro assay system that monitors drug-induced changes in multiple myocardial performance indices in real time will drastically improve the predictive accuracy of drug-induced cardiotoxicity as well as allow evaluation of cardiac function and identification of key genes or signaling pathways in cardiac tissues. The gold standard of cardiac performance indicators, load-dependent contractility (Frank-Starling curve), and other physiological parameters characterizing the contractility including energy-producing mitochondrial activity will be measured simultaneously in vitro using the EHTs (FIG. 1). To predict the human-specific cardiotoxicity, the EHTs will be developed using cardiac myocytes derived from human iPSCs or embryonic stem cells.

Engineered cardiac tissues and methods of using these tissues are provided herein. The cardiac tissues comprise or consist essentially of or consist of cardiomyocyte cells derived from a pluripotent cell, fibroblast cells and extracellular matrix components. The tissues contract coherently. In some embodiments the growth ability of the fibroblast cells is capable of being limited. Means for limiting the growth of the fibroblasts are discussed below. In some embodiments, the tissue contracts synchronously with electrical pacing by an external electrical stimulator. The engineered cardiac tissues have cardiac performance similar to normal cardiac tissue obtained from a subject or host.

Figure 2:
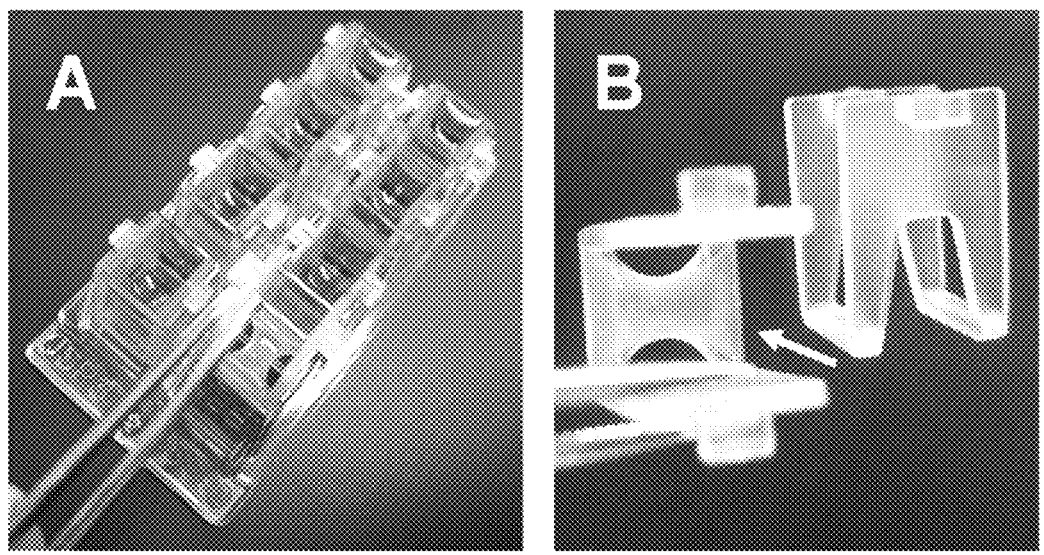
FIG. 2 is a set of photographs depicting the 8 well chamber (A) and tissue supported on a scaffold (B).
Figure 3:
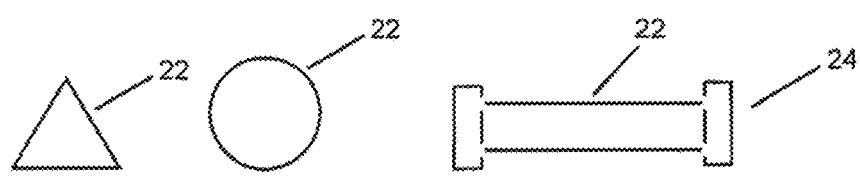
FIGS. 3A-3C shows several views of various scaffolds configurations.
Figure 3:
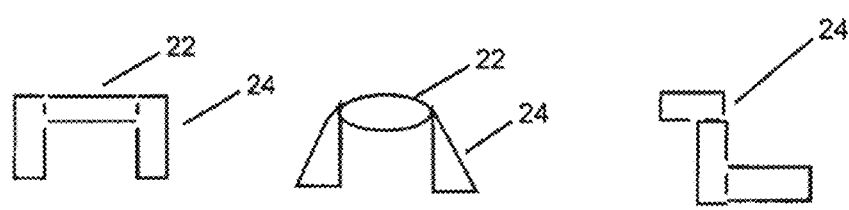
Figure 3:
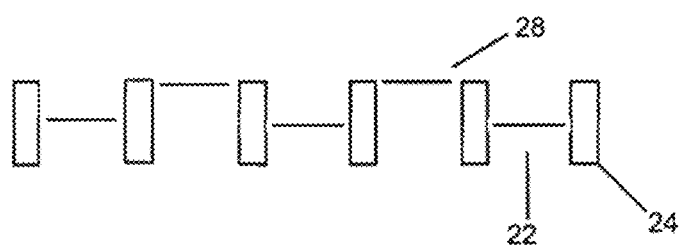
Figure 4:
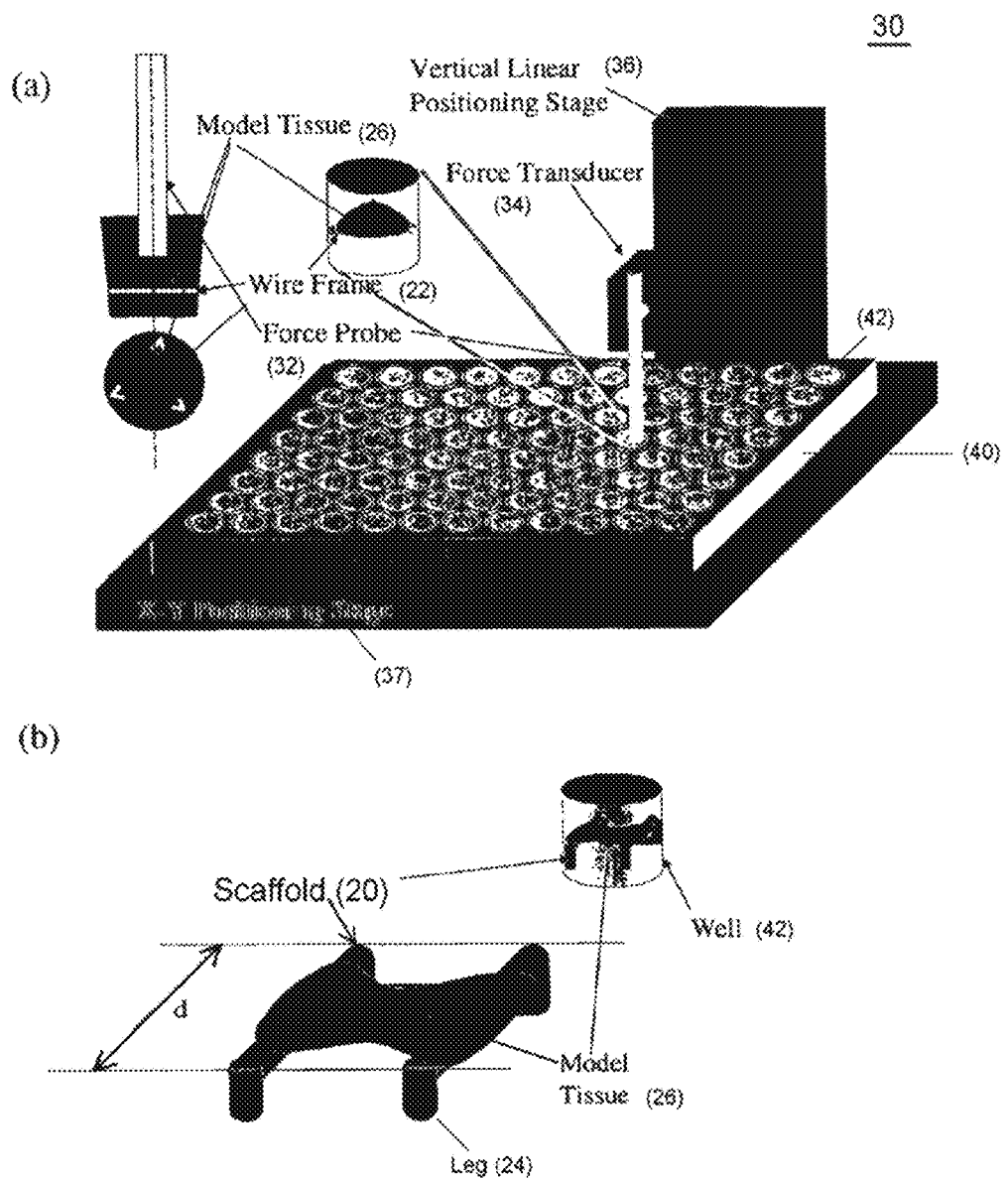
FIG. 4 is a schematic of a high throughput system (A) illustrating the use of triangular and rectangular (alternative) shape frames (B) which provide scaffold supports on which reconstituted tissues form to provide samples for assays.

The tissue may be formed on a scaffold support disposed within a well and the tissue may be suspended from the scaffold support above the bottom of the well. The tissue can be formed on a scaffold support and used for assays on the same scaffold support without a fastener to facilitate tissue adhesion. The tissue may be suspended from the scaffold support above the bottom of the well. Photographs of one embodiment of a well comprising a scaffold and tissue are depicted in FIG. 2. A schematic drawing of scaffold supports is provided as FIG. 3 and its use in at least one system for measuring force transduction is shown in FIG. 4.

The engineered cardiac or heart tissues (EHT) provided are based on cardiomyocytes derived from pluripotent cells. The pluripotent cells are suitably induced pluripotent stem cells (iPSCs) or embryonic stem cells. The cells may be derived from any suitable animal, including but not limited to, human, mouse, rat, pig, cow, dog, hamster, guinea pig, chicken or monkey cells. Methods for generating cardiomyocytes from pluripotent cells are known to those skilled in the art. Methods of transfecting or genetically engineering stem cells to either carry or express novel, non-native genes and proteins or to mutate single genes are also known to those skilled in the art. Thus, the cardiomyocytes may be engineered to express non-native proteins such as antibiotic resistance genes. The cardiomyocytes may also be engineered to lack or have decreased expression or activation of particular genes or proteins coded for by those genes. Suitably, the cardiomyocytes used to generate the tissue are fairly homogenous. Suitably the source of the cardiomyocytes contains few if any non-cardiomyocyte cells. Suitably over 90%, 92%, 95%, 98% or 99% of the cells are cardiomyocytes.

The fibroblasts used to create the EHTs may be obtained from cell lines, may be primary fibroblasts or may be derived from pluripotent cells. The fibroblasts are suitably cardiac fibroblasts and suitably they are of the same species as the cardiomyocytes used in a tissue. The fibroblasts may also be genetically engineered. Methods of genetically engineering fibroblasts are known to those skilled in the art.

Suitably the growth of the fibroblast cells is capable of being limited. The growth can be limited by any means known to those of skill in the art, including induction of senescence, inhibiting or activating a cellular protein, removing a mediator necessary for growth or even killing at least a portion of the cells. In one embodiment, the fibroblasts are sensitive to an inhibitor and the cardiomyocytes are resistant to the inhibitor. In another embodiment, the fibroblasts are auxotrophs and the media used with the tissues lacks the required nutrient for fibroblast growth. Suitably the growth and functionality of the cardiomyocytes is not significantly affected by the means of limiting fibroblast growth.

The growth of the fibroblasts may be limited by addition of a pharmacologic inhibitor. Suitably the pharmacologic inhibitor does not limit the growth or function of the cardiomyocytes. Suitable pharmacologic inhibitors include, but are not limited to, antibiotics, an inhibitor of a signaling pathway required for fibroblast proliferation, such as the ROCK kinase inhibitor, or an inhibitory RNA, such as a shRNA or iRNA. In at least one embodiment, the fibroblasts are sensitive to an antibiotic and the cardiomyocytes are resistant to the antibiotic. The cardiomyocytes may be genetically engineered to be resistant to the antibiotic. Suitable antibiotics include, but are not limited to puromycin, hygromycin and neomycin.

In another embodiment, the fibroblasts are engineered to comprise a suicide gene that can be activated to result in cell killing or inhibit further growth of the cells. For example, the fibroblasts may be transfected with the thymidine kinase gene from Herpes Simplex Virus such that the fibroblast cells become sensitive to an antiviral such as gancyclovir. Other suicide genes are known in the art, such as those described in International Patent Application No. WO1996/016183.

The fibroblasts may also be genetically engineered to allow the growth of the fibroblasts to be limited by removal of a component necessary for growth. For example the fibroblasts may be engineered to be auxotrophic for a nutrient or cellular building block, such that removal of the component from the growth media results in senescence or death of the fibroblast cells.

As used herein the extracellular matrix (ECM) components include collagen, fibrin, fibronectin, laminin and similar constituents/components and synthetic materials such as polylactic acid and polyglycolic acid. ECM may be provided via a commercially available ECM substitute such as a hydrogel like Matrigel™. The ECM components used in the tissues and methods described herein may be comprised of a single component (e.g., collagen) or may be complex (e.g., containing multiple ECM components or a complex mix of components). The ECM components may comprise a mix of natural and synthetic materials.

The EHT includes cardiomyocytes and fibroblasts. The fibroblasts can overwhelm the cardiomyocytes by replication such that the resulting tissue does not have the functional properties of cardiac tissue. Thus, the growth of the fibroblasts may need to be limited as described above, but the fibroblasts are critical for formation of a functional EHT. One means of limiting fibroblast overgrowth is by using fewer fibroblasts than cardiomyocytes to make the tissue. For example the fibroblasts may represent as little as 2%, 5%, 10%, 15%, 20%, 25%, 30%, 35%, or 40% of the original cells used to generate the tissue. The ratio of fibroblasts to cardiomyocytes in the tissues used for functional assays should be between about 0.1:1 and about 2:1. Suitably, a 1:1 ratio of fibroblasts to cardiomyocytes is used.

In some embodiments the EHTs are trabeculated to allow for more efficient transfer of media constituents into the cells and to extend the useful life of the tissue. As described in the Examples section, the tissue may be trabeculated using any of the following methods: 1) reducing the concentration of collagen and Matrigel used in forming the tissue, 2) mixing in biodegradable synthetic material with the EHT composition to introduce pores after formation of the tissue and 3) physically puncturing small holes using a needle and precision control instrument.

Figure 5:
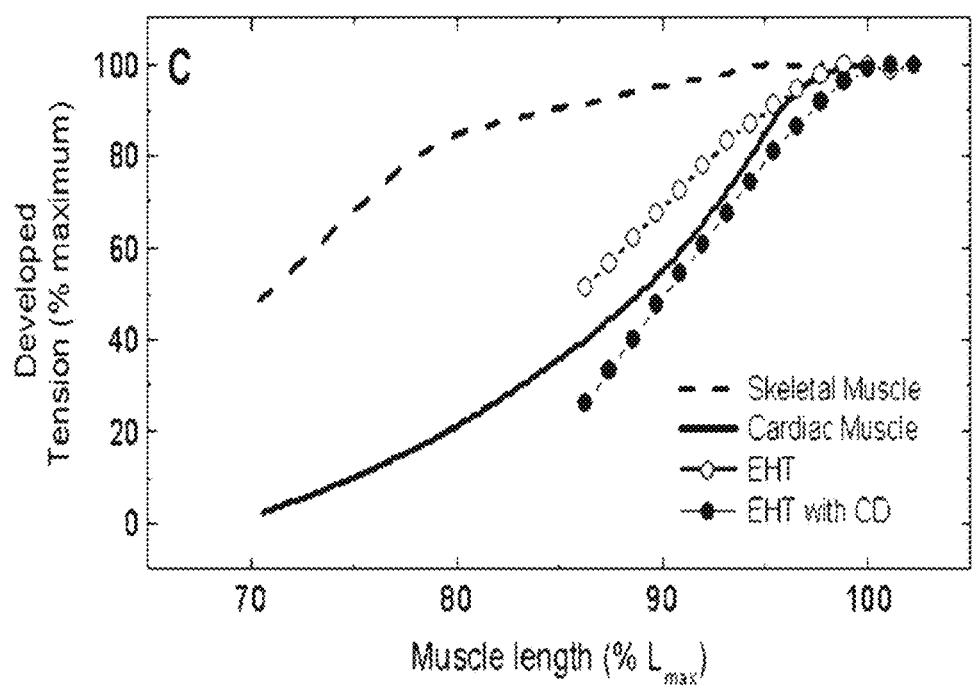
FIG. 5 is graph showing the Frank Starling relationship comparing heart tissue with engineered heart tissues.

The EHTs begin to contract coherently within a few days of formation as the fibroblasts restructure the tissue and the cardiomyocytes begin to align. The tissues can then be stimulated to contract synchronously with electrical pacing by an external stimulator such as the Dual Channel Biphasic Stimulus Isolator, Harvard Apparatus. The tissues behave similar to the left ventricle of the heart. The tissues develop a twitch force that can be measured using devices known to those of skill in the art such as the Palpator™ device (InvivoSciences, LLC). See U.S. Pat. Nos. 7,449,306 and 8,071,381. The EHTs develop a similar length-tension relationship (Frank Starling mechanism) as found in native heart tissue as shown in the Examples and at FIG. 5. When the muscle length is above 85% of that produced by maximum cardiac contraction, the cardiac tension is greater than 40% of the maximum cardiac tension. When the muscle length is above 90% of that produced by maximum cardiac contraction, the cardiac tension is greater than 50% of the maximum cardiac tension. When the muscle length is above 95% of that produced by maximum cardiac contraction, the cardiac tension is greater than 80% of the maximum cardiac tension.

The cardiac functionality of the EHT can be maintained over a relatively long period of time. In particular, the twitch force of the EHT can be maintained for more than 2 days, 4 days, 6 days, 1 week, 2 weeks, 3 weeks, 4 weeks, 5 weeks, 6 weeks, 8 weeks, 10 weeks, 12 weeks or more. Such a long lived tissue allows for long term monitoring experiments and may be more likely to detect subtle effects on the EHT or effects that only appear over time or with repeated exposure.

FIG. 4 illustrates an exemplary high throughput screening system utilizing the engineered cardiac tissues described herein. The screening mechanism depicted is one optional method in which the tissues may be used. The system shown in FIG. 4 is described in U.S. Pat. Nos. 7,449,306 and 8,071,381.

A frame, generally designated as reference numeral (22), e.g., a triangular frame, made of stainless steel wire provides a scaffold (20) on which reconstituted tissue (26) forms in the Examples. In this illustration, the wells (42) are slightly tapered toward the bottom and the frame is securely positioned about 1 mm above the bottom of the well. The non-polymerized solution of collagen containing cells and appropriate cell culture media as described is poured into the wells, filling them to a level 3 mm above the bottom (FIG. 4a). The 96-well plate (40) may be incubated at 37° C. with 5% $CO_2$. During incubation, the cells self-assemble into a bio-artificial tissue and compress the collagen matrix by squeezing out liquid thereby reducing the total volume by about ten-fold.

Without the scaffold or wire frame, the reconstituted tissue contracted into a small sphere floating in the tissue culture medium. The collagen matrix can be compressed into different shapes using different frame shapes such as a circle or rectangle as depicted in FIG. 3. One of skill in the art will appreciate that a wide array of shapes could be used. Other wire frame shapes, such as those shown in FIG. 4b and FIG. 3, produced tissue strips with different widths and shapes. Any shape frame (22) can be used to form a scaffold (20), including but not limited to, circular, rectangular, triangular, pentagonal, hexagonal, or other higher order polygons. The scaffold may also be formed of more than one member. For example, the scaffold (22) could be formed of two parallel members spaced apart with or without one or more perpendicular member connecting them (FIG. 4b and FIG. 3).

The scaffolds are suitably made of any non-porous, biocompatible material, such as metal, nonmetal, or plastic. In the Examples, the scaffold was made of stainless steel or plastic (polycarbonate, polystyrene, or others). One of skill in the art will appreciate that other materials including, but not limited to, glass or polystyrene may also be suitably used to produce the scaffold.

In accordance with the present invention, cells self-assemble to form a tissue model conforming to the shape of the scaffold or support. In forming, the tissue overlays the members of the scaffold, spanning the space between the members. For example, on a triangular wire frame, the cells form a membrane spanning among the three edges, which is illustrated in FIG. 4a. The scaffold or wire frame in the Examples was about 1 mm in diameter, but frames may suitably have smaller or larger cross-sectional diameters. Suitably, the scaffold is made up of one or more members with cross-sectional diameters between about 100 µm and about 2 mm. The frame is comprised of generally cylindrical, tubular, or elongate members that allow the tissue to form around the members such that the tissue overlays the members. The members comprising the frame are suitably somewhat rounded to minimize ripping of the tissue when force is applied. For example, members with a rectangular cross-section could be utilized if the edges were rounded such that the tissue did not tear when force was applied. The members are suitably made of a non-porous material and have a cross-sectional diameter of less than about 2 mm, suitably about 1 mm.

The bio-artificial tissue forms a membrane structure spanning a horizontal cross-sectional space between or across the members comprising the frame. The tissue is supported above the bottom of the well by the scaffold support. The tissue is suitably substantially parallel to the bottom of the well. The horizontal cross-sectional space the bio-artificial tissue spans is suitably larger than 10 µm, but can be as large as the well (42) allows, suitably the tissue spans a space between about 100 µm and about 5 mm, more suitably between 1 mm and 4 mm. A typical bio-artificial tissue depicted in FIG. 2 is approximately 4×4×0.8 mm and formed in a 8×8 mm square chamber. (The shape of chamber was modified for viewing the sample in the figure.).

The frame (22) is suitably supported above the bottom (43) of the well (42). The frame (22) may be supported by the side of the well by using tissue culture plates with tapered wells. The frame may be manufactured as part of the well. As depicted in FIG. 1, the MC-8™ wells have substantially parallel stainless steel rods penetrating the sides of the wells to form the scaffold. Alternatively, the scaffolds may be plastic and made such that the scaffold is an insert which hangs from the top of the well as shown in FIG. 2. The scaffold supports may also be formed as a unitary feature of the wells.

Alternatively, the frame may be supported above the bottom of the well by using specially designed plates with built-in scaffolds attached to the side of the well or with wells having ledges on which the frame rests. In another alternative embodiment, the scaffold may include a frame with at least one leg (24) attached to the frame (22) to support the frame above the bottom of the well. The number of legs (24) required to support the frame will vary depending on the shape of the frame. FIG. 4b depicts a scaffold with 4 legs, but scaffolds may be designed with fewer or more legs as depicted in FIG. 3. The legs (24) may be used to support the frames (22) by projecting down from the frame and touching the bottom of the well (42) or the legs (24) may project upwards from the frame (22) and support the frame of the scaffold (20) by anchoring the scaffold to the top (45) of the well (42). For example, the leg (24) may have a small hook structure at the end that allows the scaffold (20) to hang from the top of the well (FIG. 3(b)). Although the frame (22) of the scaffold is supported above the bottom of the well, the exact distance is not critical as long as the tissue can be bathed in media. Suitably, the scaffold is at least about 0.5 mm above the bottom of the well, more suitably the scaffold is at least about 1.0 mm above the bottom of the well.

FIG. 2 depicts a prototype multi-well plate (4) comprising scaffolds (20). The 8-well plate was machined from a polycarbonate bar (25×60×10 mm) using a tabletop CNC mill (Sherline Products Inc., Vista, Calif.). The 8 square wells (42) of 8×8 mm contained 2 stainless steel bars (22) (1 mm diameter). The centers of the stainless steel bars were located 2 mm above the bottom of the well and 2 mm from the side of the well such that the 2 bars were 4 mm apart. A microscope coverslip (No. 1 thickness, Fisherbrand) was used to seal the bottom of each well using silicon glue (Dow Chemical Co., Midland, Mich.) to facilitate microscopic imaging.

For ease of use in a high throughput system using a multi-well plate format, the scaffolds (20) may be joined together by a connector (28) in groups including but not limited to, 2, 4, 8, 12 or 96 scaffolds as depicted in FIG. 3C. By joining scaffolds (20) together in groups, the scaffolds can be readily positioned in a multi-well plate (40). The connectors (28) may be made to be readily separable, e.g., such that a quick tugging motion will break the connection and allow the user to customize the number of scaffolds used. The scaffolds and bio-artificial tissue system described herein may also be adopted for use by one of skill in the art in any multi-well plate, including but not limited to, 6 well, 8 well, 12 well, 24 well, 48 well, 192 well or 384 well plates.

As seen in the Examples below, a porous support material, or other fastener, such as a Velcro fastener or burr, was not needed to facilitate tissue adhesion even to the non-porous stainless steel surfaces of the wire frame used. The collagen was compressed to a greater extent at the outer portion of the membrane or tissue strip and allowed the tissue to be suspended on the scaffold without the need for a fastener. Therefore, this outer portion of the membrane can withstand the stress produced by the cells and prevents ripping the bio-artificial tissue off from the wire frame.

The tissues described herein can be used in a variety of methods including those described in U.S. Pat. No. 7,449,306 and U.S. Patent Application Publication Nos. US 2008/0038812, US2009/0068701 and US2011/0118143. Additional methods of measuring cardiac performance include, but are not limited to cardiac contractility, Frank-Starling curves, twitch force, effects of cyclic stretch on contractility, viability, mitochondrial membrane potential, ATP concentration, free radical production, oxygen consumption, gene or protein expression, cell signal transduction, myocyte size, tissue organization, or degree of fibroblast activation.

Figure 6:
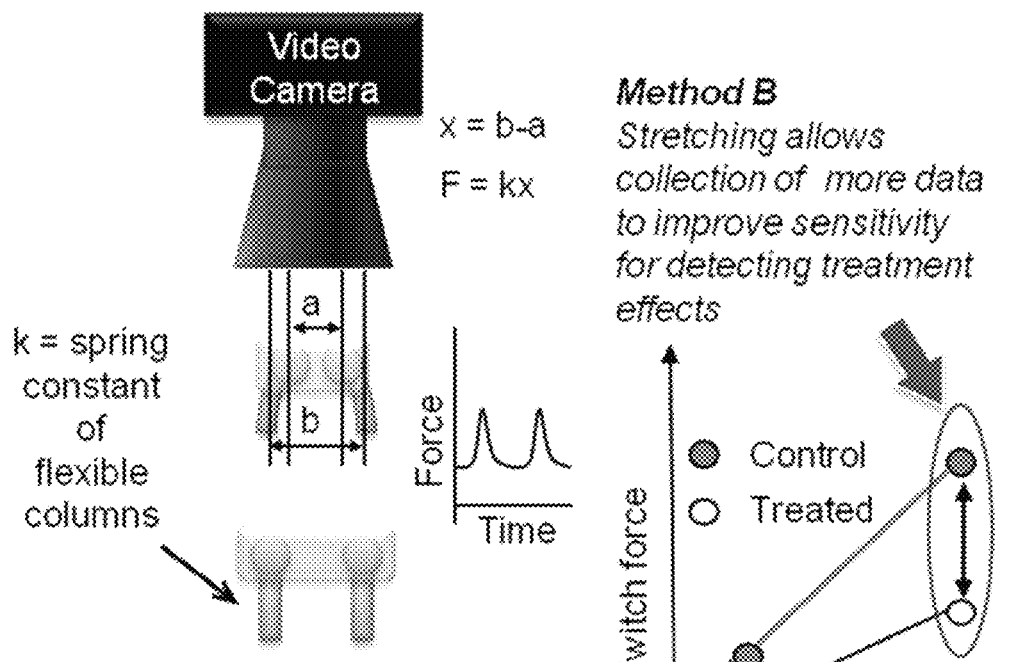
FIG. 6 is a set of schematics showing comparisons of force measurement protocols via image analysis (A) and force sensor methods (B).
Figure 6:
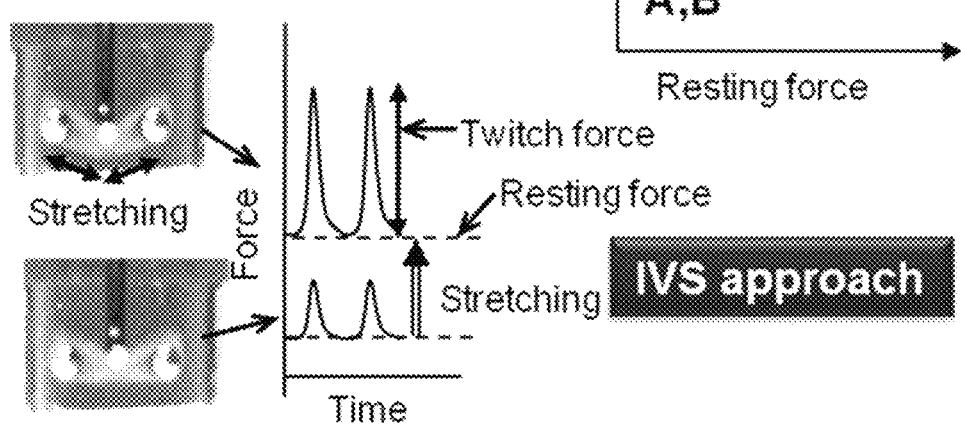

Our force sensor approach measures EHT contractility at multiple stretch-levels (FIG. 6) while the image-based assays (FIG. 6) can measure only a single stretch-level. The spring constant of flexible columns holding EHTs constrains its detection dynamic range. Too strong or too weak contraction to bend the columns will not be registered effectively. We optimized to perfect the dynamic range of force sensors to suit for the EHT contractility assessments.

The tissues described herein may be used in methods to evaluate the effects of an agent on cardiac performance. The methods include contacting the EHTs described herein with the agent and comparing the cardiac performance of the tissue after contact with the agent. Treated or contacted with includes, but is not limited to, exposed to, incubated with, contacted with, placed in contact with, injected with, and transfected with. Those of skill in the art will appreciate a wide variety of methods may be used to measure or evaluate the cardiac performance of the contacted tissue. In one embodiment a plurality of tissues may be contacted with varying concentrations of the agent. The comparison of cardiac performance may then allow one to create a dose response profile for the tissue's response to the agent.

Agents useful in the methods include but are not limited to pharmaceuticals, biomolecules or bioactive agents such as nucleic acid and protein based agents including small molecules, antibodies, aptamers, inhibitory RNAs, such as shRNAs, and the like. The amount of agent(s) provided to the tissues is an effective amount which is generally from an amount in nanomolar quantity to an amount of about 100 millimolar. An effective amount is that amount which is sufficient to elicit a response from or by a tissue.

The cardiac performance of the tissue after contact with an agent may be compared to that of a control. Those of skill in the art will be able to appreciate the range of suitable controls available for each use of the methods. The comparison may be to the same tissue prior to contact with the agent or to a parallel tissue not contacted with the agent. Suitably cardiac performance is measured quantitatively such that the comparison to the control can be quantified. The methods are useful to identify agents that may be cardiotoxic. For example, the tissues described herein may be contacted with an agent and the cardiac performance of the tissues may be compared to similar tissues after contact with an agent with known cardiotoxicity.

In another embodiment the methods and tissues described herein may be used to elicit the mechanism of action of an agent or the mechanism of cardiotoxicity of an agent. In this embodiment an inhibitory RNA may be used to inhibit a protein of interest in certain cells of the tissue (i.e. fibroblasts, cardiomyocytes or both). The protein of interest may be a target of an agent with known cardiotoxicity, suspected cardiotoxicity or unknown cardiotoxicity. This method could also be used to evaluate whether a protein known to be involved in a particular disease such as cancer is a good drug target or whether down-regulation or inhibition of the normal function of the target protein has inherent cardiotoxicity associated with such treatment. Such analyses could be useful in intelligent drug design strategies.

The following examples are meant to be illustrative only and are not meant to limit the scope of the claims. Each reference or patent application referred to herein is hereby incorporated by reference in its entirety.

EXAMPLES

EHT Assay 1: Contractility.

EHTs were fabricated with $1.75\text{-}2\times10^6$ cardiomyocytes/mL using MC-8™ system (InvivoSciences, LLC). The cardiomyocytes were obtained from neonatal rats and guinea pigs, or embryonic mice or chicken. Viable and spontaneously twitching EHTs were generally obtained by day 10 after fabrication. The EHTs were electrically stimulated (60 mV, 1 Hz) during mechanical testing. The mechanical properties of EHTs using the Palpator™ device (InvivoSciences, LLC). This automated device positions a force probe directly above the center of each well (FIG. 7A-i) and moves it vertically in two (or more) steps (FIG. 7A-ii, -iii) to stretch twice the EHT to 3.7% and 7.7% longitudinally. Cardiac twitch (systolic) force and resting (diastolic) force were measured during each step for 30 and 60 s. Similar to native biological tissues, stretching the tissue induced rapid increases in force, followed by slow relaxation. The slope of line connecting the two points of twitch and resting force relations (FIG. 7B) exhibited the EHT's muscle specific length-tension relationship, i.e., the Frank-Starling mechanism. The peak rate at which the cardiac twitch force changes (FIG. 7C) also indicated the contractility (FIG. 7D) of the EHT much like the $dP/dt_{max}$ of left ventricles measured by pressure catheters.

EHT Assay 2: Optical Biomarker.

The bottoms of the 8-well chambers were sealed with glass coverslips so that EHT cells could be observed using various optical instruments including microscopes and fluorescence plate readers in real time or after fixations. To demonstrate this capability, the cardiomyocytes' mitochondrial membrane potential (MMP) was measured by pre-incubating the EHTs with a potentiometric dye, tetramethylrhodamine ethyl ester (TMRE) that binds negatively charged mitochondria. Mitochondria produce ATP via the electrochemical/osmotic gradient (~180 mV) generated and maintained by the electron transport chain. Therefore, highly charged mitochondria produce ATP to support cardiac contractions.

Using a fluorescence plate reader (Synergy™ HT, BioTek U.S., Winooski, V T), we simultaneously measured TMRE's fluorescent signal (543 nm excitation/605±16 nm emission) and EHT contractions to determine the coupling between MMP and cardiac contractility. After a short (15-min) administration of 900 µM DNP (2,4-dinitrophenol), a potent uncoupler of MMP (FIG. 7F), to the EHTs MMP was reduced and cardiac contraction stopped (FIG. 7E). Although treatment with 450 µM DNP attenuated the MMP, the cardiac twitch force was not reduced significantly. This demonstration supports the ability of this system to simultaneously measure multiple biological indicators and cardiac contractility to evaluate the physiological activity of cardiomyocytes under different conditions.

Cardiotoxicity Assessment.

Figure 8:
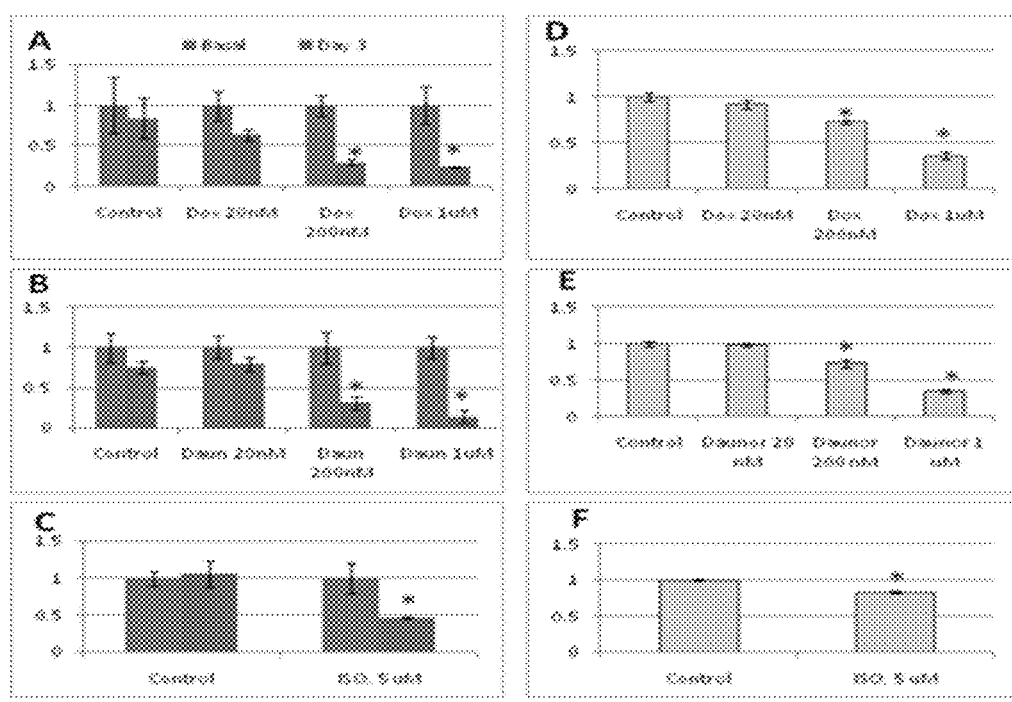
FIGS. 8A-8F is a set of graphs depicting the effects of daunorubicin (20 nM, 200 nM, and 1 uM) and isoproterenol (5 uM) on EHTs. Cardiac contractility is depicted in FIG. 8A-C after a 3 day incubation with and without each drug. Cellular viability (FIG. 8D-F) was determined after the contractility assay. *=statistical significance. All data normalized to controls.
Figure 9:
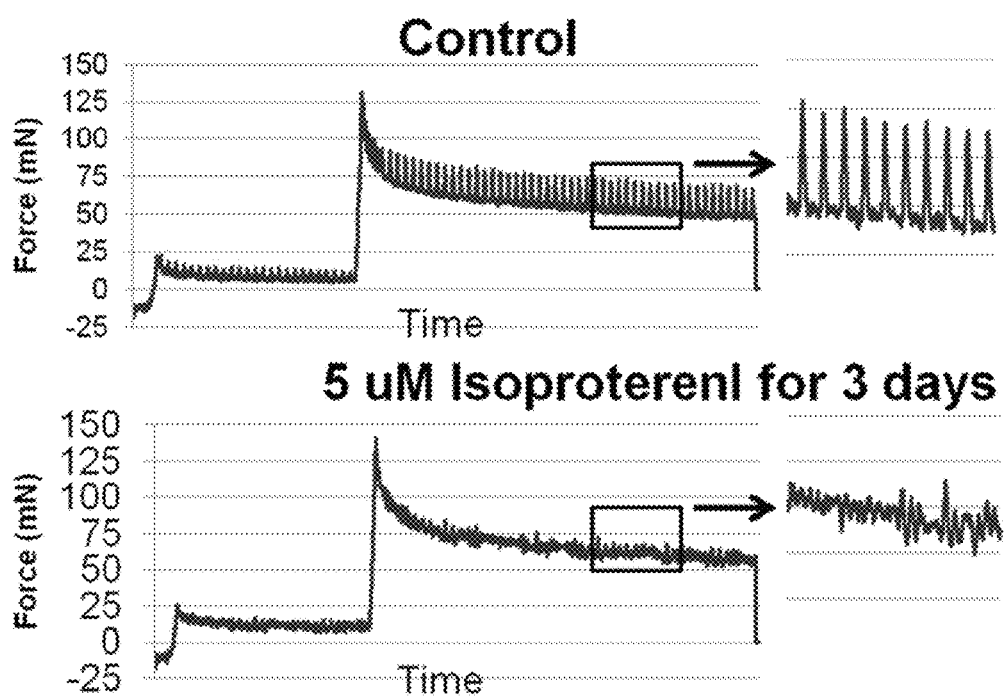
FIG. 9 is a set of graphs showing isoproterenol (5 uM for 3 days) induced arrhythmias in EHT. Control (top) and treated (bottom) clearly show arrhythmias in the treated EHTs only.

To validate the ability of our assay system to assess cardiotoxicity, we profiled the effects of anti-cancer agents (doxorubicin and daunorubicin) and beta-adrenoceptor agonist (isoproterenol), which are known to cause cardiotoxicity in clinical and experimental applications. As a non-toxic control, we selected the beta-adrenoceptor agonist (dobutamine) and an immunosuppressant drag (cyclosporin A), for which cardiac toxicity has not yet been described. Adverse effects of cyclosporin A include liver and kidney dysfunction. After a 3-day incubation with doxorubicin (20 nM, 200 nM, or 1 µM) the EHTs were measured again and their viability was determined. Doxorubicin significantly decreased tissue contraction (FIG. 8A), but did not affect the variables affecting matrix stiffness. The observed decline in cardiac function correlated with reduced cell viability as measured by the MTT assay (FIG. 8D). As with doxorubicin, we observed reduced cardiac tissue contraction after incubating the EHTs with another anti-cancer drug, daunorubicin (FIG. 8B). Again, impaired contractility correlated with decreased cellular viability as measured by the MTT assay (FIG. 8E). High doses of isoproterenol (a non-selective beta 1- and beta 2-adrenoreceptor agonist), can cause arrhythmia and have cytotoxic effects, resulting in heart failure in in vivo animal experiments. We confirmed the toxic effect of 5 µM isoproterenol by measuring the decreased twitch force (FIG. 8C) and corresponding decrease in cellular viability (FIG. 8F). Additionally, we observed arrhythmias after isoproterenol treatment (FIG. 9 bottom) compared to the control EHT (FIG. 9 top).

The experiments with proarrhythmic drugs and known cardiotoxins demonstrate the power of using the Palpator system for screening cardiac drugs. The knowledge gained will help to detect cardiotoxic drugs in future screenings of unknown compounds and may enable discovery of new properties of well-known chemical agents.

Identification and Analysis of Protein Effects on Cardiac Function

In addition to developing technology, our long-term goal is to identify small molecules or disease target molecules that regulate development of cardiac fibrosis. Rho kinase (ROCK) is suggested to be one of the key regulators in the development of cardiac fibrosis. However, two isoforms of ROCK have been identified and are known to be involved in signaling pathways that are important for maintaining normal physiology. Therefore, we hypothesized that regulation of cardiac fibrosis is isoform-specific. Using shRNAs that are specifically designed to down-regulate ROCK1 or ROCK2, we identified isoform-specific profibrotic phenotypes regulated by ROCKs.

Figure 10:
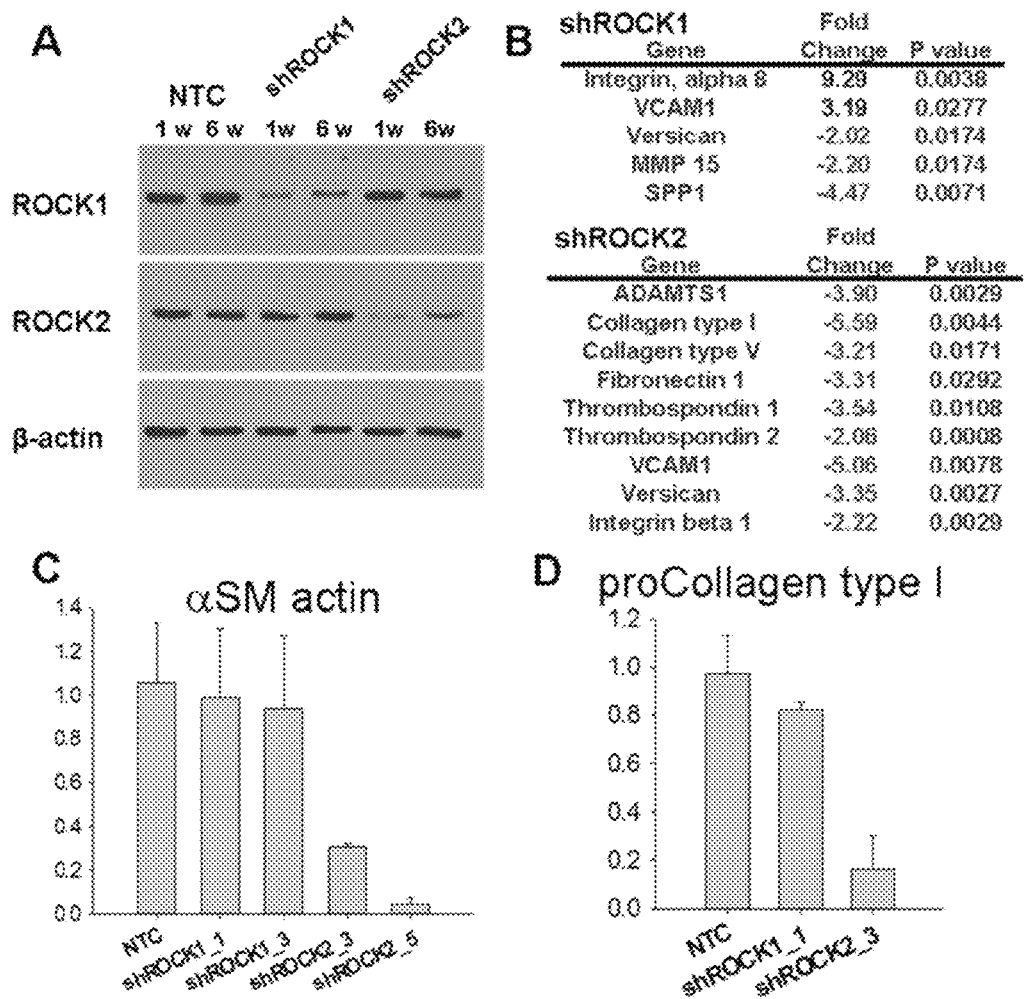
FIGS. 10A-10D shows ROCK-isoform specific regulation of cardiac fibrosis regulation.

In this study with shRNA and the ROCK isoforms, we identified at least two shRNA sequences for each ROCK isoforms that specifically down-regulate expression of ROCK1 or 2 (FIG. 10A). shRNA sequences were recommended by OpenBiosystem or other software to design efficient shRNA sequences. Candidate sequences are screened and selected for efficiency by transfecting the human dermal fibroblasts and confirming sufficient knockdown of protein expression. Viral particle concentration was titrated. Normally lenti-viral MOI (multiplicity of infection) between 1-5 was used for infection without viral cytopathic effect. The shRNA plasmid can be transfected using an electroporator such as Neon Transfection System (Invitrogen). After applying these shRNAs, we analyzed changes in gene expression in the extracellular matrix and cell adhesion proteins (96 genes) using a PCR array (SABiosciences, Frederick, Md.). Many profibrotic genes were down-regulated only by shROCK2-treated samples (FIG. 10B). In addition, ROCK2-knockdown decreased the expression of alpha smooth muscle (αSM) actin, which is a myofibroblast biomarker found only in scar and wound tissue (FIG. 10C). Gene expression analysis confirmed the down-regulated protein expression (FIG. 10D). Thus the tissues described herein may be used to understand basic biology of tissues as well.

Fabricating Engineered Tissues using Human Cardiac Cells Derived from Human iPS Cells.

Cardiac tissue patches developed from human embryonic stem cells have been shown to twitch by measuring periodic changes in patch size, but the twitch force developed by the patches has never been reported. Our goal was to establish human EHTs that produce cardiac twitch force sufficient for analyzing drug-induced cardiotoxicity as well as other parameters of cardiac function. Although EHTs made using pure populations of CMs derived from mouse ES cells do not twitch coherently, adding cardiac fibroblasts to the CMs has made it possible to fabricate EHTs that develop measurable twitch force as demonstrated below. It is necessary to use the proper combination of cardiac fibroblasts with highly purified CMs derived from human iPSCs (or embryonic stem cells) to yield human EHTs that produce substantial cardiac twitch force. We will be fabricating the EHTs using both CMs derived from antibiotic resistant human iPSCs, and human cardiac fibroblasts (antibiotic-sensitive, commercially available from Lonza). The growth of cardiac fibroblasts will be regulated systematically to optimize the fabrication and culture conditions for human EHTs to maintain twitch contraction for at least 2-3 weeks. Successful development of human EHTs will provide a powerful tool for detecting potential drug-induced cardiotoxicity caused by compounds intended to treat human diseases and for analyzing the underlying molecular mechanisms of the observed effects.

EHTs-Compacted by Fibroblasts Developed Synchronous Beating

Figure 11:
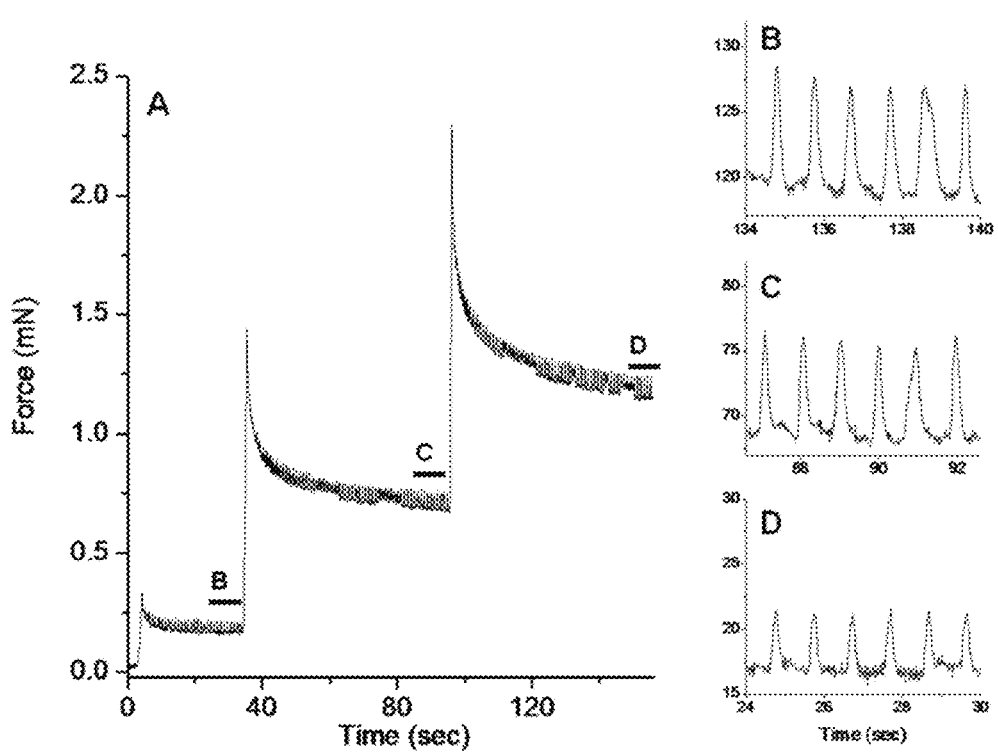
FIGS. 11A-11D is a set of graphs showing the Frank-Starling length tension response in EHTs fabricated using mouse ES derived cardiomyocytes.

We fabricated EHTs using CMs derived from mouse ES cells (Cor.AT, Axiogenesis) that express a puromycin resistance-GFP reporter gene fusion driven by a cardiac-specific (αMHC) promoter. These Cor.AT CMs ($1.75 \times 10^6$) were co-cultured with cardiac fibroblasts (FBs) in a 1:1 ratio (See Asnes, C. F., et al., *Reconstitution of the Frank-Starling mechanism in engineered heart tissues*. Biophys J, 2006. 91(5): p. 1800-10) for developing a coherently contracting EHT. The EHTs were compressed by the FBs from a loose ($6 \times 6 \times 3.5$ mm$^3$) hydrogel into a compacted (~$3 \times 2 \times 0.5$ mm$^3$) coherently contracting tissue in 5-7 days. After the compaction, the puromycin sensitive FBs were eliminated or their viability reduced by applying puromycin (5 µM) to prevent FB overgrowth. The CMs embedded in collagen without FBs formed cell-aggregates that beat independently and incoherently so that the tissue did not twitch as a whole. The remodeling capacity of FBs was needed to fabricate compressed 3D tissues that can generate cardiac contraction synchronously. Upon achieving synchronous contraction, the cardiac twitch force was measured using the Palpator. The EHTs exhibited a similar length-tension relation (FIG. 11, Frank-Starling mechanism) seen in native cardiac tissues. The data indicate our ability to fabricate EHTs that display Frank-Starling behavior from mouse ES-cell derived CMs. We expected that application of a similar protocol to fabricate EHTs with iPSC-derived CMs should produce similar cardiac contractility since individual CMs derived from human ES cells, iPSCs, and native rat hearts produced equivalent degrees of cardiac contractility. Our results showing similar results for human ES cells is below.

Optimization of the Concentration and Growth of Human Cardiac Fibroblasts

Figure 12:
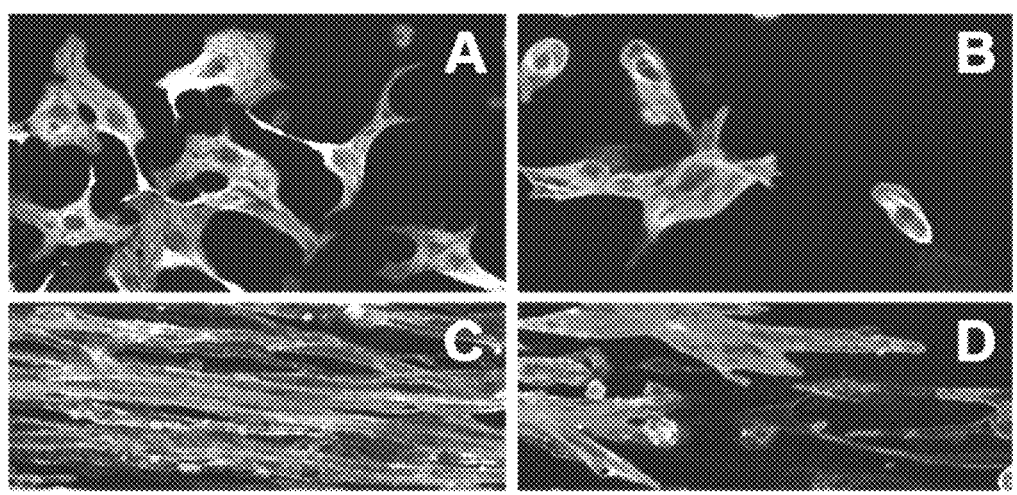
FIG. 12 is a set of photographs sowing hypertrophy promoted by fibroblast conditioned media. In two dimensional cultures grown with fibroblast conditioned media the cardiomyocytes spread more (A) than those cultured in control medium (B) supplemented with 10% FBS. Cardiomyocytes in EHTs cultured with conditioned medium were extended and made more connections with other cardiomyocytes (C) than those in control medium (D).

The successful fabrication of mouse EHTs was achieved by doping the right amount of cardiac FBs to promote compaction of loosely distributed CMs in the hydrogel. Fibroblasts support the alignment of CMs parallel to the direction of developed force (perpendicular to the supporting bars). In addition, the conditioned medium secreted by cardiac fibroblast has been shown to induce CM spreading in 2D and 3D (FIG. 12). Therefore, cardiac FBs will be beneficial especially for the initial development of EHTs. However, FB over-growth could damage CM survival and contractile force development. Using the puromycin selection marker, the ratio of FBs to CMs will be selectively controlled to maintain optimal contractile function of the EHTs. The FB growth curve will be determined against different concentrations of puromycin. The timing (1-5 days) of puromycin addition after EHT fabrication will affect the EHT development. Another important parameter is the initial ratio of FBs to CMs. In adult hearts the number of FBs is nearly the same as CMs. The load-dependent cardiac contractility will be used as a criterion for successful EHT fabrication. Varying the puromycin selection and initial ratio of CM to FBs, the optimal conditions with which to obtain the highest cardiac twitch force with least resting force can be obtained and indicate minimum FB overgrowth.

Improve CM Survival to Produce Highly Contractile Human EHTs by Artificial Trabeculation.

Improving CM survival requires increasing diffusivity of molecules throughout the EHT to improve exposure of the CM to $O_2$ and nutrients while fibroblasts are compacting the construct. The porosity of the matrix will be enhanced by 1) reducing the concentration of collagen and Matrigel, 2) mixing in biodegradable synthetic material with the current EHT composition to introduce pores and 3) physically puncturing small holes (~100 µm diameter) in the EHT after fabrication. Biomade Technology Foundation (Netherlands) manufactures a biodegradable low-molecular-weight hydrogelator (LMWH) whose compatibility with CMs has been tested by Biomade using two dimensional cell culture systems (i.e. coating tissue culture dishes with LMWH and growing cells). Biomade makes various types of biodegradable LMWH including those that can degrade themselves upon brief exposure to pH 5. The LMWH has been shipped to IVS and we are fabricating engineered tissue to test their properties including rate of degradation by pH change and effects of low pH on CMs and fibroblasts. After or during the EHT compression LMWH will be degraded to generate porous structure resembling the trabeculation of endocarium.

Alternatively to generate small holes in the EHT tissues, we will use the Palpator. A sterile syringe needle (I.D. 89 µm) attached vertically to the xyz arm of the Palpator will be inserted into freshly fabricated EHTs with x-y position accuracy of ±10 μm. While the needle is puncturing the tissue, a negative pressure is applied to suck out the hydrogel and make a 2 mm deep hole every 200-300 μm. Improved diffusivity resulting from this quasi-trabeculation will be measured by fluorescence recovery after photobleaching (FRAP) using our published protocol (Kalyan, C. V. and et al., *Analysis of the diffusion of Ras2 in Saccharomyces cerevisiae using fluorescence recovery after photobleaching*. Physical Biology. 7(2): p. 026011). Alexa 546 conjugated-dextrans (3,000 and 10,000 MW) will be used for the FRAP analysis. From the fabrication techniques discussed above, we will identify the methods that best enhance molecular transport and improve local availability of nutrients. The normally prepared nontrabecular EHTs will serve as controls for this study. When an optimum protocol for fabricating the artificial trabeculae is established, the EHT cell survival and phenotypic characterization experiments will be performed to assess the improvements in cell viability and functionality resulting from trabeculation. Trabeculation is expected to generate many parallel tissue-strips but homogenize the cell alignment throughout the constructs.

Mixing of medium and continuous agitation of the entire culture chamber may enhance transport in trabeculated tissue and further enhance viability and longevity of the EHTs. Application of low flow perfusion through the EHT will also be tried if simple agitation does not generate sufficient transport. In addition, survival of myocytes in the 3D environment will be optimized by monitoring the metabolic activity of mitochondria after changing the various culture conditions as described below.

Additionally, IVS has launched a tissue stretcher (FIG. 13A) to apply constant cyclic stress while EHTs are developing. The cyclic stretch induces CM hypertrophy (FIG. 13C) to improve its contractility as compared to its control (FIG. 13B). The stretching will be applied to improve our EHT functions.

Identify Potential Mechanisms of Drug Induced-Cardiotoxicity via Analyzing the Effects of Knocking Down the Drug Target Enzyme in EHTs.

FDA approved drugs in general are thought to be "well-tolerated" for cardiovascular safety. However, little is known about the true cardiovascular toxicity of these approved drugs including their effects on left ventricular function. The enzyme mTOR (mammalian target of rapamycin) is the target molecule that several recently approved cancer drugs inhibit. In addition to cancer growth, mTOR plays important roles in muscle growth and cardiac hypertrophy. A recent study of mTOR using a conditional cardiomyocyte-specific knockout mouse revealed the detailed mechanisms by which the mTOR knockout induces reduction of cardiac functions leading to heart failure and death. The data present a unique opportunity to understand how closely the cardiac performance profiled using EHTs resembles that observed using the mTOR KO mouse.

We will use the published data in the mTOR KO mouse to objectively analyze the data obtained using our EHT-based assay system. Comparison between data obtained using EHTs and the KO mouse model will serve as a benchmark of expectations and limitations of the in vitro assay system.

Monitoring Mitochondrial Activities

Figure 14:
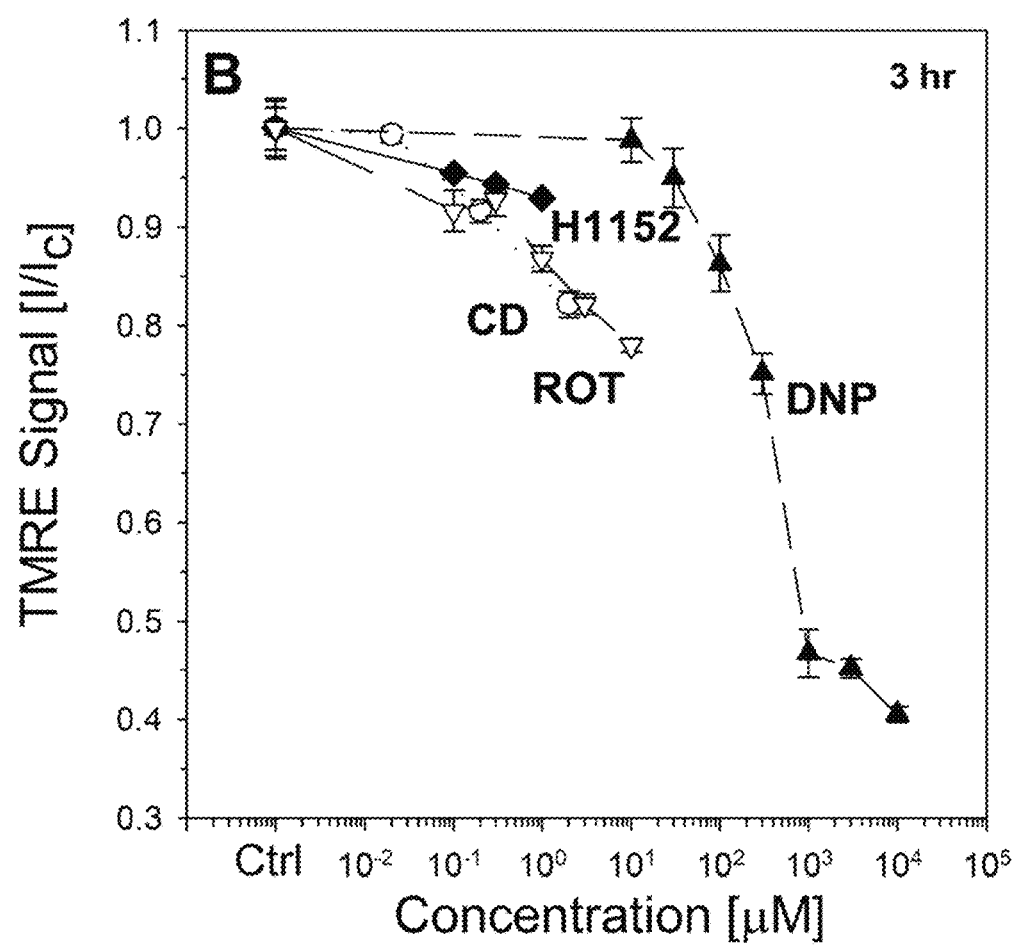
FIG. 14 shows a graph of the dissipated mitochondrial potential after increasing doses of DNP.

Drug-induced cardiotoxicity often damages mitochondrial metabolic activity. We have developed additional assays for quantifying the mitochondrial membrane potential (MMP) of EHTs using the cationic potential metric dye tetramethylrhodamine ethyl ester (TMRE), and we are also assessing EHT viability using 3-(4,5-Dimethylthiazol-2-yl)-2,5-diphenyltetrazolium (MTT). An automated microplate reader was used to measure fluorescence or optical absorbance of these dyes. With these assays, we successfully screened for a small molecule that modulates cellular and tissue contractility without altering MMP and viability of cells (details in Lam, V. and T. Wakatsuki, *Hydrogel Tissue Construct-Based High-Content Compound Screening*. Journal of Biomolecular Screening, 2011. 16(1): p. 120-128.). Four test compounds were assayed: Rho kinase inhibitor (H1152), cytochalasin D (CD), 2,4-dinitrophenol (DNP), and rotenone (ROT). Treating rat EHT with DNP dissipated MMP with $EC_{50}$ of 340 μM (FIG. 14). Assays to assess mitochondrial activity and metabolic parameters such as ATP concentrations, $O_2$ consumption and free radical production have been measured using similar techniques, see e.g. Lam, V. and T. Wakatsuki, *Hydrogel Tissue Construct-Based High-Content Compound Screening*. Journal of Biomolecular Screening, 2011. 16(1): p. 120-128; Sedlic, F., et al., *Monitoring mitochondrial electron fluxes using NAD (P)H-flavoprotein fluorometry reveals complex action of isoflurane on cardiomyocytes*. Biochimica et Biophysica Acta (BBA)—Bioenergetics, 2010. 1797(10): p. 1749-1758; and Sedlic, F., et al., *Mitochondrial depolarization underlies delay in permeability transition by preconditioning with isoflurane: roles of ROS and Ca2+*. American Journal of Physiology—Cell Physiology, 2010. 299(2): p. C506-C515. Our EHT-based assay system can obtain high-content information about the metabolic activities underlying the mechanisms that regulate cardiac functions and drug-induced cardiotoxicity.

Fabricate EHTs with CMs Whose Drug Target Molecule, mTOR, is Conditionally Inhibited by shRNA.

To understand the role of mTOR in maintaining cardiac functions, mTOR expression will be knocked down using an shRNA lenti-viral system. We achieved successful knock down (KD) of ROCK1 or 2 for at least 6 weeks (FIG. 10, above), which is essential for monitoring myogenic development of EHTs taking more than 2 weeks. We will first establish a protocol to select the optimal shRNA sequence constructs purchased from OpenBiosystems (Huntsville, Ala.). To conditionally KD mTOR under doxycycline (Dox, ~2 ug/ml), we will construct an appropriate vector, also available from OpenBiosystems. Before constructing the Dox-inducible vector ~5 different shRNA sequences targeting mTOR will be analyzed to select at least two sequences that are most effective without inducing cytotoxic effects detected by cell viability assays. We already have an optimized empty vector control and non-targeting control directed against a scrambled vector. To select shRNA transfected CMs from non-transfected CM and FBs, antibiotic (hygromycin) selection systems incorporated into shRNA vectors are available from Clontech.

Figure 7:
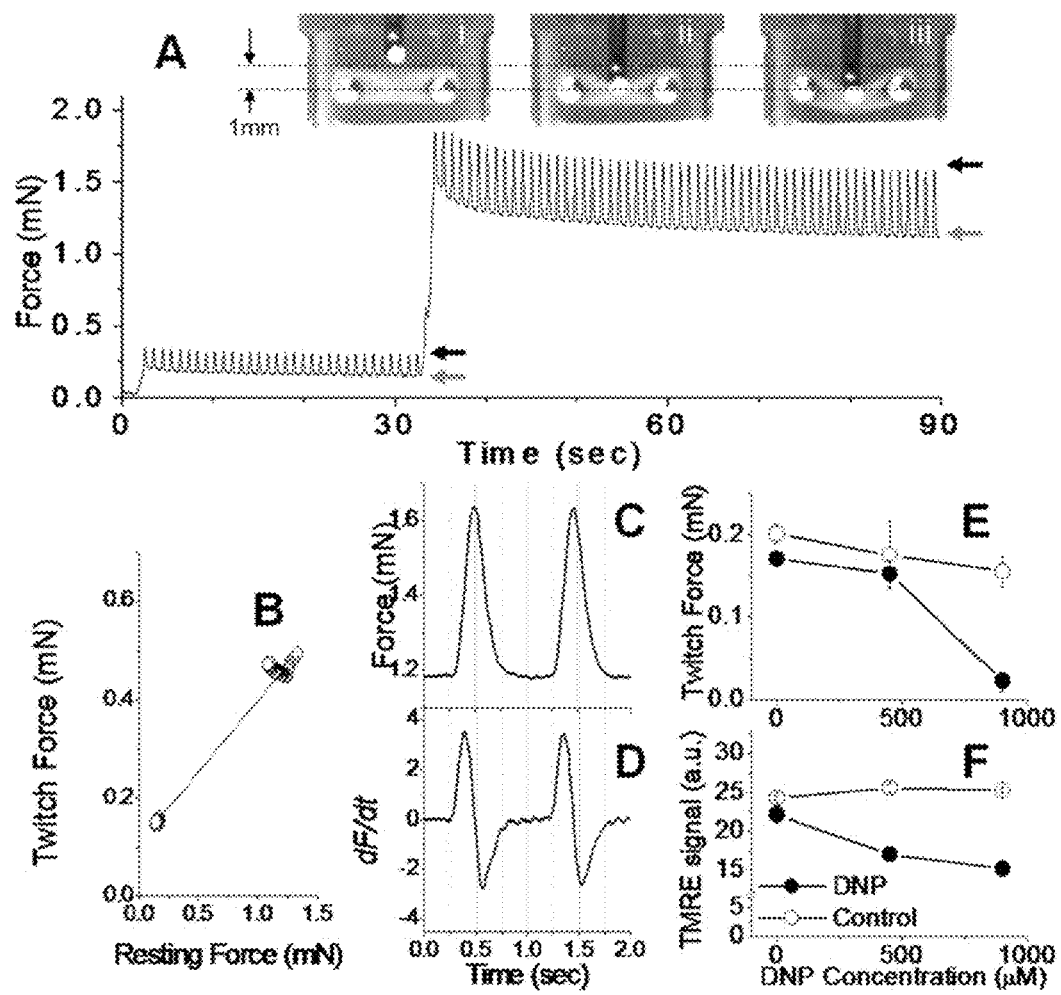
FIGS. 7A-7F is a set of figures showing the EHTs reconstitute cardiac physiology.
Figure 13:
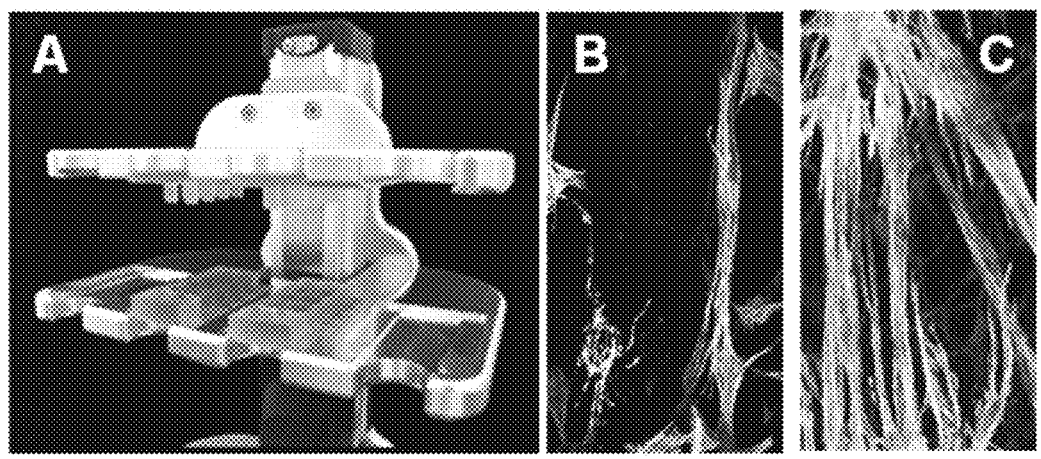
FIG. 13 shows a photograph of a tissue stretcher (A) and photographs of normal cardiomyocytes in an EHT (B) and after cyclic stretch for 5 days (C).

Drug-induced and mTOR KD-induced changes in cardiac performance of EHTs will be monitored by measuring 1) cardiac contractility, 2) mitochondrial activities, 3) the effects of cyclic stretch (mechanical loading) on cardiac contractility, mitochondrial activities, gene/protein expression and activation of signaling pathways. As described previously, cardiac contractility will be measured using the published protocol as well as the modified protocol used to measure cardiac contractility of EHTs using the Palpator (FIG. 7). The contractility of untreated controls will be compared to those treated with a drug or to mTOR KD EHTs. In our experience n=8 will provide sufficient statistical significance (ANOVA analysis) to detect the expected reduction in contractility (FIG. 8). Mitochondrial membrane potential will also be monitored using a published protocol discussed above. Because of the importance of mTOR in regulating the pressure overload response, cardiac performance as well as change in myocyte size, and degree of fibroblast activation will be monitored after exposing the EHTs to cyclic stretches using the stretcher (FIG. 13). We will start with a 3 day continuous stretching protocol to obtain an increase in CMs in EHTs (FIG. 13).

The system can also be used to investigate signaling pathways in the tissues. Phosphor-specific antibodies able to recognize active enzymes including Akt (pT450, pT308, pS473), 4E-BP1(pS65), S6K1 (pT389) will be used to elucidate the differences in mechanisms. Appropriate concentrations of rapamycin, sirolimus, temsirolimus, and everlimus will be used to inhibit mTOR.

Co-Culturing FBs with Cor.AT CMs and Eliminating FBs with Puromycine Treatment.

Figure 15:
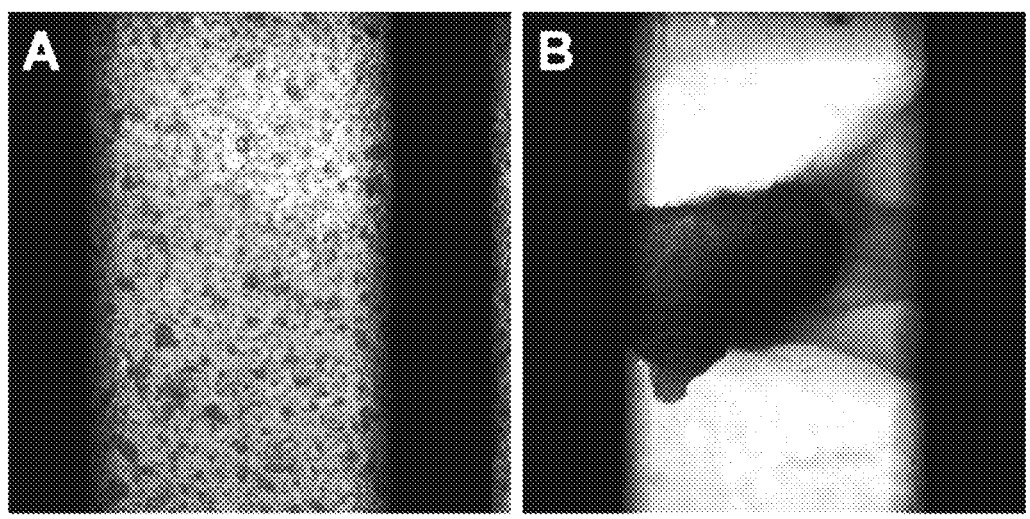
FIGS. 15A-15B is a set of photographs showing the effects of myofibroblasts (mFBs) on remodeling and compression of engineered heart tissues (EHTs).

An increasing density of cardiomyocytes (CMs) in the EHT constructs promoted intercellular contacts to form a synchronously contracting EHT while myofibroblasts (mFBs) remodeled and compressed the constructs. However, an overgrowth of mFBs limited survival of CMs. By regulating the mFB proliferation, cardiac contractility of EHTs without mFBs was maintained at least 10-50% longer than those with mFBs. This was demonstrated using mouse embryonic stem cell (ESC)-derived CMs (Cor.AT cells) that express a puromycin resistance-GFP reporter gene whose expression was driven by a cardiac-specific (αMHC) promoter. The Cor.AT CMs ($1.75 \times 10^6$) that were embedded without mFBs in 3D hydrogels formed aggregates and beat independently, and the tissue did not change its size (FIG. 15A). The Cor.AT CMs ($1.75 \times 10^6$) were co-cultured with mFBs in a 5:1 ratio using previously published method and developed a coherently beating EHT. The EHTs with mFBs were compressed from a loose ($6 \times 6 \times 3.5$ mm$^3$) hydrogel into a compacted (~$3 \times 2 \times 0.5$ mm$^3$) tissue in 5-7 days (FIG. 15B). Varying numbers of mFBs were mixed with CMs (e.g., 0.1:1, 0.5:1 up to 1:1) to fabricate EHTs. The mFB increased degrees of 1) EHT compaction, 2) CM density, 3) CM alignment (elongation of CMs in parallel with its direction of contraction, 4) CM viability and metabolic state, and 5) maintenance of EHT contractility.

Figure 16:
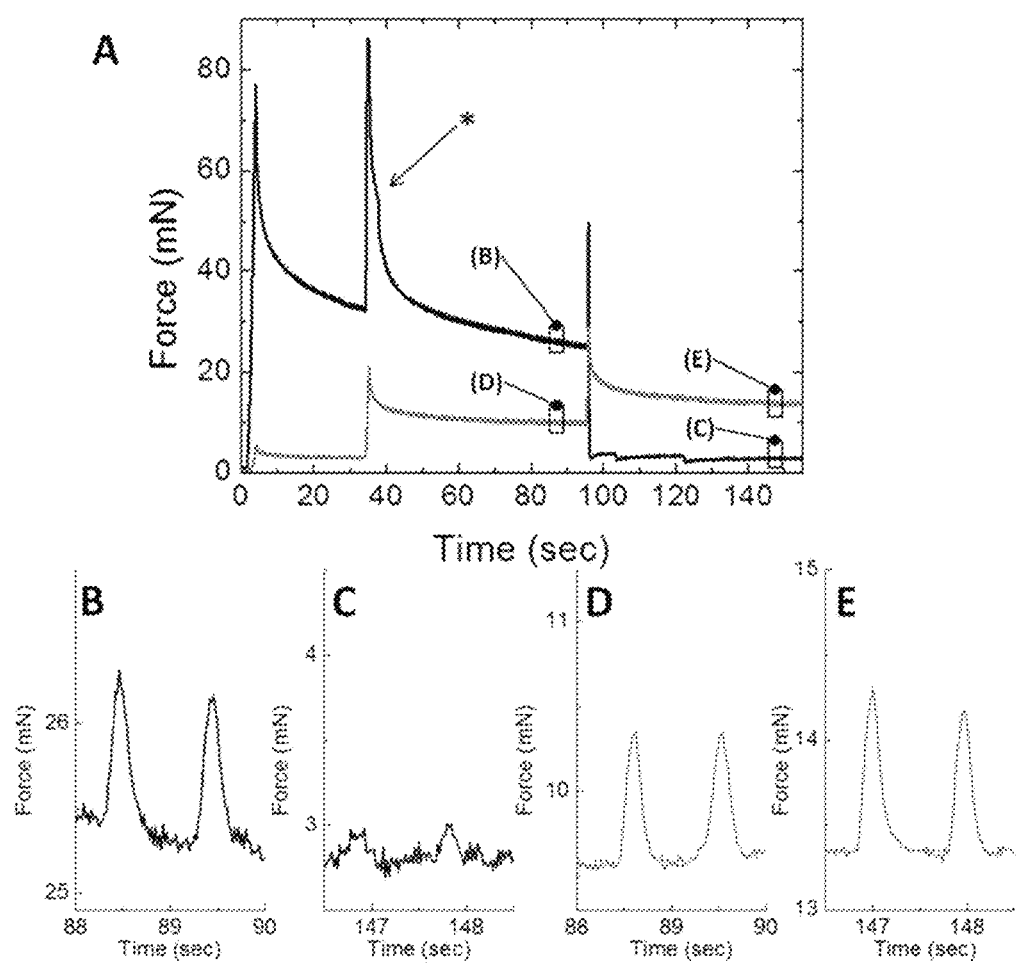
FIGS. 16A-16E is a set of graphs showing the effect of mFBs on cardiac contractility, stiffness and integrity of EHTs. The EHTs were fabricated by mixing Cor.AT myocytes with human cardiac myofibroblasts. A puromycin (10 µM) treatment selected puromycin-resistant myocytes and eliminated mFB in the EHTs. EHTs with and without mFBs were stretched 4, 8 and 10% for their mechanical measurements. (A), a baseline tissue force of EHTs with mFBs (black line) was nearly ten-fold higher than that of EHTs without mFBs (gray line). An increasing tissue-stretch resulted in tearing the EHT with mFBs (*). Detail cardiac twitch force profiles in the boxed regions are shown as cardiac contractility of EHTs with mFB under 8% (B) and 10% (C) and of EHTs without mFB under 5% (D) and 10% (E).

The mFBs were eliminated by applying puromycin (10 mM). EHTs without eliminating mFBs showed nearly ten times higher baseline tissue force than that of mFB eliminated EHTs with purimycin treatment (FIG. 16A). In stress-relaxation responses of EHTs after a quick stretch (8%), the EHTs with mFB (non-puromycin treated) showed a much larger step response than EHTs without mFBs (puromycin treated). This indicates that EHTs with mFBs are significantly stiffer than EHTs without mFBs. Because of the overly stiffened EHTs with mFBs, the tissue broke during the stress-relaxation test. EHTs without mFBs showed similar levels of cardiac contraction (FIG. 16B, D) with a significantly lower baseline force. The broken EHTs with mFBs registered very little cardiac twitch force (FIG. 16C). Whereas the EHTs without mFBs continued to increase its cardiac contractility by stretching more (i.e., Frank-Starling mechanism) (FIG. 16D,E). The timing of puromycin addition was also varied to develop tissues with various degree of fibrosis. The size of fibrotic region was enlarged by extending the period of EHT culture without puromycin because of the mFB overgrowth.

Human Cardiomyocyte Tissues Derived from Human Embryonic Stem Cells

Figure 17:
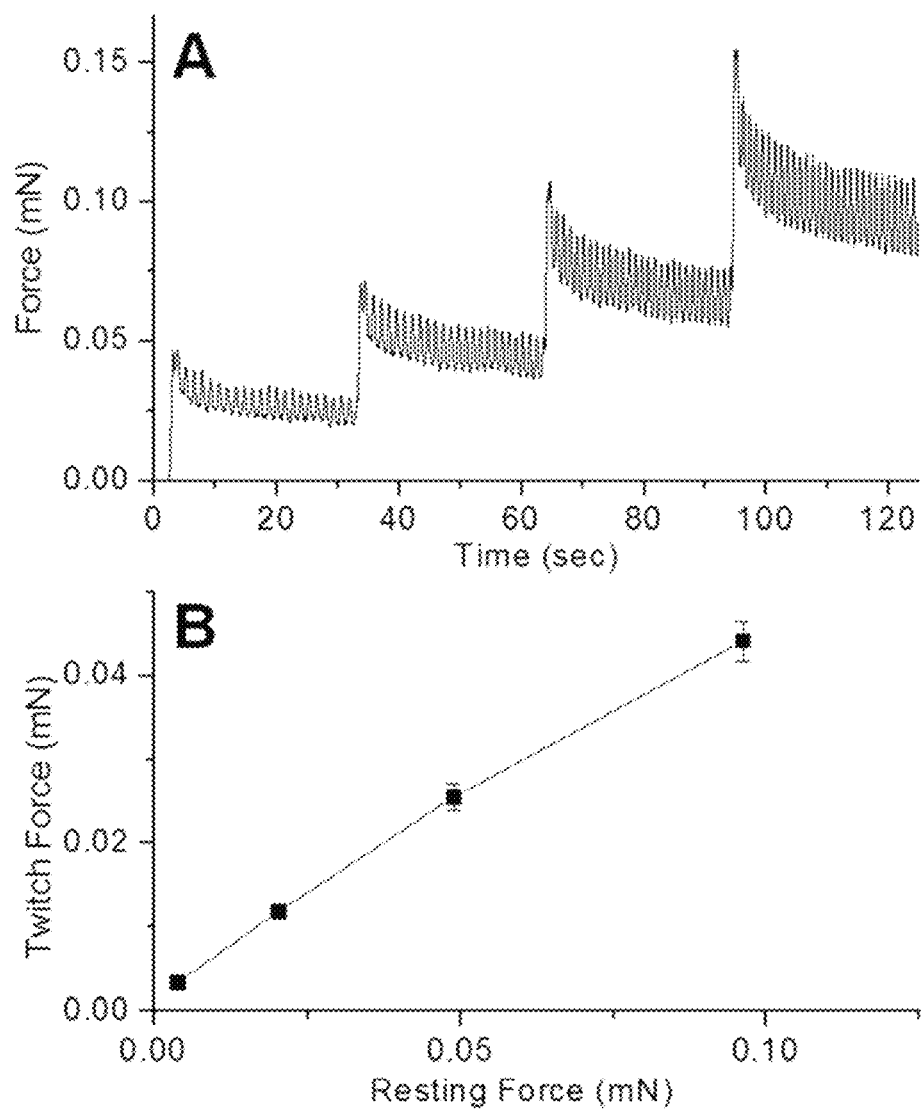
FIGS. 17A-17B is a set of graphs showing the measurements of cardiac twitch force developed by human engineered heart tissues fabricated with cardiomyocytes derived from human embryonic stem cells. Increasing cardiac twitch force recorded by increasing a length of EHT (A). (B) shows a plot of twitch force vs. resting force recorded in (A).

Human CMs ($2 \times 10^6$ cells/ml) derived from human embryonic stem cells were embedded in 3D hydrogels and formed a coherently beating EHT. The EHTs with FBs were compressed from a loose ($6 \times 6 \times 3.5$ mm$^3$) hydrogel into a compacted (~$3 \times 2 \times 0.5$ mm$^3$) tissue in 5-7 days. Stretching human EHTs increase baseline and cardiac twitch force similarly to those observed from EHTs fabricated with Cor.AT cells (FIG. 17B). Resting and cardiac twitch force increased as increasing tissue lengths.

I claim:

1. An engineered cardiac tissue comprising human cardiomyocyte cells comprising a transgene encoding a protein that results in resistance to a pharmacologic inhibitor wherein said transgene is operably linked to a cardiac-specific promoter, cardiac fibroblast cells and an extracellular matrix component, wherein the ratio of fibroblasts to cardiomyocytes is between 0.1:1 and 2:1, and wherein the tissue contracts coherently.

2. The tissue of claim 1, wherein the tissue contracts synchronously with electrical pacing by an external electrical stimulator.

3. The tissue of claim 1, wherein the fibroblasts are derived from a pluripotent cell.

4. The tissue of claim 1, wherein the cardiomyocyte cells are derived from a cell selected from an iPSC (induced pluripotent stem cell) or an embryonic stem cell.

5. The tissue of claim 1, wherein the tissue has a similar length-tension relationship as found in native cardiac tissues.

6. The tissue of claim 1, wherein when the muscle length is above 85% of that produced by maximum cardiac contraction, the cardiac tension is greater than 40% of the maximum cardiac tension.

7. The tissue of claim 1, wherein the twitch force of the tissue is maintainable over more than two weeks.

8. The tissue of claim 1, further comprising endothelial cells or precursors of endothelial cells.

9. The tissue of claim 1, wherein the pharmacologic inhibitor comprises an antibiotic.

10. The tissue of claim 1, wherein the tissue further comprises a scaffold support disposed within a well, and the tissue is suspended from the scaffold support above the bottom of the well and wherein the tissue is formed on the scaffold support without a fastener to facilitate tissue adhesion.

11. The tissue of claim 10, wherein the scaffold support is a wire or plastic frame.

12. The tissue of claim 1, wherein the twitch force of the tissue is maintainable over more than four weeks.

13. The tissue of claim 1, wherein the fibroblast cells are added separately from the human cardiomyocyte cells to form the tissue.

* * * * *